United States Patent [19]
Berglund et al.

[11] Patent Number: 5,897,908
[45] Date of Patent: *Apr. 27, 1999

[54] COMPOSITION AND METHOD FOR PRODUCING A SALTY TASTE

[75] Inventors: Kris A. Berglund, Okemos; Hasan Alizadeh, East Lansing, both of Mich.

[73] Assignee: Board of Trustees operating Michigan State University, East Lansing, Mich.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/593,160

[22] Filed: Feb. 1, 1996

Related U.S. Application Data

[63] Continuation-in-part of application No. 08/376,395, Jan. 23, 1995, Pat. No. 5,527,959.
[51] Int. Cl.$^6$ ...................................................... A23L 1/237
[52] U.S. Cl. ........................... 426/649; 426/656; 426/804
[58] Field of Search ...................................... 426/648, 649, 426/804, 656; 562/562

[56] References Cited

U.S. PATENT DOCUMENTS

| 1,874,055 | 8/1932 | Liebrecht . |
| 2,824,008 | 2/1958 | Perri et al. . |
| 2,829,056 | 4/1958 | Kemmerer . |
| 3,015,567 | 1/1962 | Hause et al. . |
| 3,993,795 | 11/1976 | Mauron et al. . |
| 5,145,707 | 9/1992 | Lee . |
| 5,173,323 | 12/1992 | Omari . |
| 5,176,934 | 1/1993 | Lee . |
| 5,229,161 | 7/1993 | Turk . |

*Primary Examiner*—Arthur L. Corbin
*Attorney, Agent, or Firm*—Ian C. McLeod

[57] ABSTRACT

A physical mixture which consists essentially of compositions of lysine monohydrochloride and potassium chloride alone or admixed with small amounts of succinic acid, in particular weight ratios, and which has a salty taste comparable to table salt (sodium chloride). The mixture masks the bitter aftertaste of the potassium chloride and can provide dietary lysine which is an essential amino acid.

10 Claims, No Drawings

COMPOSITION AND METHOD FOR PRODUCING A SALTY TASTE

CROSS-REFERENCE TO RELATED APPLICATIONS

This application is a continuation-in-part of application Ser. No. 08/376,395, filed Jan. 23, 1995, now U.S. Pat. No. 5,527,959.

GOVERNMENT RIGHTS

This application was funded under United States Department of Agriculture Contract No. 90-34189-5014 Sub of 4501. The United States Government has certain rights under this application and any patent issuing thereon.

BACKGROUND OF THE INVENTION (1) Summary of the Invention

The present invention relates to table salt (sodium chloride) substitute compositions and their method of use. In particular, the present invention relates to physical mixtures of lysine monohydrochloride and potassium chloride, and optionally succinic acid which produce a salty taste and which unexpectedly closely parallels the taste of table salt.

(2) Description of Related Art

Numerous compositions have been described by the prior art as table salt substitutes. Illustrative are U.S. Pat. Nos. 1,874,055 to Liebrecht; 2,824,008 to Perri et al; 2,829,056 to Kemmerer; 3,015,567 to Hause et al; 3,993,795 to Mauror et al; 5,145,707 to Lee; 5,173,323 to Omari; 5,176,934 to Lee and 5,229,161 to Turk. Some of the compositions use lysine mono- or dihydrochloride and potassium chloride mixed together (Omari and Kemmerer); however, there are additional ingredients, particularly glutamates which produce allergic reactions (asthma, headaches, etc. in certain people) and do not enhance taste or sodium chloride, which is to be avoided in salt-free diets.

OBJECTS

It is therefore an object of the present invention to provide novel potassium chloride lysine monohydrochloride mixtures, preferably with a small amount of succinic acid which closely parallels the taste of table salt. Further, it is an object of the present invention to provide a method for using the compositions. Further, it is an object of the present invention to provide the compositions which are easily prepared as an admixtures. These and other objects will become increasingly apparent by reference to the following description.

DESCRIPTION OF PREFERRED EMBODIMENTS

The present invention relates to an edible composition having a salty taste which consists essentially of an admixture selected from the group consisting of (1) lysine monohydrochloride and potassium chloride, and (2) the lysine monohydrochloride, the potassium chloride and succinic acid each of which are food grade, wherein the weight ratio of the lysine monohydrochloride to potassium chloride is between about 1 to 9 and 3 to 2 and wherein the ratio of lysine monohydrochloride to succinic acid is between about 3 to 1 and 13 to 1 and the composition has a pH between about 5.5 and 6.3.

The present invention also relates to a method for imparting a salty taste to a food which comprises providing an edible composition in the food which consists essentially of an admixture selected from the group consisting of (1) lysine monohydrochloride and potassium chloride, and (2) the lysine monohydrochloride, the potassium chloride and succinic acid which are food grade, wherein the ratio of the lysine monohydrochloride to potassium chloride is between about 1 to 9 and 3 to 2 and wherein the ratio of lysine monohydrochloride to succinic acid is between about 3 to 1 and 13 to 1 and the composition has a pH between about 5.5 and 6.3.

The composition is easily prepared by simple mixing of the ingredients. In order to mask the bitter aftertaste of the potassium chloride there must be between 10% to 60% of the lysine monohydrochloride. When crystals of lysine monohydrochloride are physically mixed with crystals of potassium chloride, the resulting mixture has the appearance of, and taste intensity of, table salt, without the characteristic taste of the potassium ion. Lysine monohydrochloride can also be co-crystallized with potassium chloride from a solution in which they are soluble (such as water) to produce a salty crystalline mixture. The succinic acid produces a more salty taste in amounts between about 0.1 and 10 percent by weight in the composition. In the most preferred compositions the weight ratio of lysine monohydrochloride to potassium chloride is between 2 and 3 to 7. When succinic acid is present, the weight ratio of lysine monohydrochloride to potassium chloride is 2 and 2.99 to 7 and the succinic acid is included in an amount between 0.1 and 10 percent by weight of the composition.

Lysine is an essential amino acid and thus is a dietary supplement. Potassium chloride is commonly used as a salt substitute to avoid sodium intake. Succinic acid is a common food acid. Thus, the composition fulfills dietary as well as taste needs.

The following are illustrative Examples of the compositions of the present invention.

EXAMPLE 1

Table 1 shows the results of taste tests by a taste panel of 3 people of various compositions incorporating lysine monohydrochloride (LysMhc) lysine monohydrate (Lysmh) potassium chloride (KCl) and an acid (HCl) or base (KOH).

TABLE 1

| Salt name | Molar Ratio of Lys/Cl/K | Solution comp. | Sol. pH | Taste |
|---|---|---|---|---|
| 1 | 2:4:2 | Lysmhc + KCl | 5.55 | Salty+++ |
| 2 | 2:3:1 | Lysmhc + KCl | 5.66 | Salty-acid |
| 3 | 2:2:1 | Lysmhc + Lysmh + KCl | 9.34 | Salty |
| 4 | 4:3:1 | Lysmhc + Lysmh + KCl | 9.48 | Salty-sweet |
| 5 | 2:2:1 | Lysmhc + KOH | 9.50 | Salty-metallic |
| 6 | 2:6:2 | Lysmhc + KCl + HCl | 1.00 | Acidic |

*The salt+ tastes saltier than salty and salty− tastes less saltier than salty.
** The water used was double distilled water.

A crystallized dry salt product composed of Lysmhc and KCl (1) with a molar ratio of 2:4 was found to possess the desired salty taste.

EXAMPLE 2

Table 2 shows the results of taste tests by a taste panel of 3 people for various mixtures of lysine monohydrochloride (Lysmhc) and KCl mixtures as dry salts and in solution.

TABLE 2

| weight % Lysmhc/KCl | Dry Mixture | Sol./2 g water | pH |
|---|---|---|---|
| 0/100 (25%) | Irritates | Irritates | 7.62 |
| 10/90 | Salty++++* | Salty++++ | 6.23 |
| 20/80 | Salty+++ | Salty++++ | 6.21 |
| 30/70 | Salty++ | Salty+++ | 6.12 |
| 40/60 | Salty++ | Salty+++ | 6.01 |
| 50/50 | Salty+ | Salty+ | 5.99 |
| 60/40 | Salty | Salty | 5.97 |
| 70/30 | Salty- | Salty+ | 5.87 |
| 80/20 | Salty-- | Salty+ | 5.83 |
| 90/10 | Salty--- | Salty-- | 5.71 |
| 100/0 (33%) | Salty-sweet | Salty-sweet | 5.75 |
| 100% dd** Water | — | — | 5.70 |

*The salt+ tastes saltier than salty and salty– tastes less saltier than salty.
**double distilled water.

As can be seen from Table 2 mixtures including 10 to 60% of the lysine monohydrochloride with potassium hydrochloride had the desired taste both in dry form and in solution. These mixtures also had an acid pH between about 5.5 and 6.3 depending upon the amount of lysine monohydrochloride.

EXAMPLE 3

Table 3 shows different concentrations of a thirty weight percent (30%) lysine monohydrochloride to potassium chloride mixture (dry) mixed which is then dissolved in water used in taste tests by a taste panel of 3 people.

As can be seen, the mixture can be used in an amount up to about 30% by weight in water to produce the desired salty taste.

TABLE 3

| 30 wt % Lys/KCl Cont. in water | pH | Taste | Comment |
|---|---|---|---|
| 10 | 6.04 | salty | Clear sol. |
| 20 | 6.02 | salty+ | Clear sol. |
| 30 | 6.02 | Salty++ | Clear sol. |
| 40 | 5.90 | Irritates | Saturated |
| 25% (100% KCl) | 7.62 | Irritates | Clear sol. |
| 25% (100% NaCl) | 7.11 | Standard | Blurred sol. |

No other amino acid tested (including glutamic acid, glutamic acid monohydrochloride, glycine, glycine monohydrochloride, and lysine monohydrate) provided the masking of the potassium taste. The optimal concentration of lysine monohydrochloride in the mixture was about thirty percent (30%) by weight in Example 3 based upon taste tests.

EXAMPLE 4

A preference test was conducted in which 38 panelists participated and tasted four dry samples in random order. The samples were:

1. 70/30 wt % potassium chloride/crystalline lysine monohydrochloride, which is the subject of the current application.

2. Commercially available MORTON SALT SUBSTITUTE (containing potassium chloride, fumaric acid, tri- and mono-calcium phosphate).

3. Example 1 of U.S. Pat. No. 2,829,056 (containing lysine dihydrochloride, mono-potassium glutamate, potassium chloride and tricalcium phosphate).

4. Regular table salt.

The results of this test indicated the composition No. 1 of the invention was preferred to No. 2 and No. 3. The ranking of Samples No. 1, No. 2 and No. 3 were 61, 75, and 86, respectively, with the lowest number being preferred. The ranking was determined as follows: There was statistically difference at the 95% level between No. 1 and No. 3 (U.S. Pat. No. 2,829,056), but the difference between No. 1 and No. 2 was not statistically significant.

EXAMPLE 5

Taste trials were performed to assess the intensity of the composition No. 1 of the invention in aqueous solution. In these trials a fifth sample was added to those of Example 4.

5. Same as No. 1 with 10% succinic acid added.

A 4% solution was prepared of each sample and the rank scores were 16, 49, 50, 55, and 55 for samples No. 4, No. 5, No. 2, No. 3 and No. 1, respectively. This test indicates that the samples No. 1 and No. 5 were about 50% the intensity of regular table salt.

EXAMPLE 6

Succinic acid (SA) was added to physical mixtures of potassium chloride (KCl) and lysine monohydrochloride (LysMhc). The results are shown in the following Table 4.

TABLE 4

| Wt % KCl/LysMhc/SA | Dry Mixture Taste | 4% Solution Taste |
|---|---|---|
| 70/30/00 | salty | very mild salty |
| 70/15/15 | very acidic, irritates | very acidic, irritates |
| 70/20/10 | very acidic | acidic |
| 70/25/05 | salty acidic | salty acidic |
| 70/27.5/2.5 | very good salty | mild salty |
| 45/45/10 | salty acidic | very little saltiness |

These data indicate that there is a taste improvement by addition of a small amount of succinic acid. The ratio of lysine monohydrochloride to succinic acid that gives this advantage is 10:1 as in application Ser. No. 08/376,395, filed Jan. 23, 1995. Preferably between about 2.5 and 2.9 percent of the composition is succinic acid and the remainder is potassium chloride.

It is intended that the foregoing description be only illustrative of the present invention and that the present invention be limited only by the hereinafter appended claims.

We claim:

1. An edible composition having a salty taste which consists essentially of an admixture selected from the group consisting of (1) lysine monohydrochloride and potassium chloride, and (2) lysine monohydrochloride, potassium chloride and succinic acid, each of which are food grade, wherein the weight ratio of lysine monohydrochloride to potassium chloride is between about 1 to 9 and 3 to 2, the weight ratio of lysine monohydrochloride to succinic acid is between about 3 to 1 and 13 to 1, and the composition has a pH between about 5.5 and 6.3.

2. The composition of claim 1 wherein the weight ratio of lysine monohydrochloride to potassium chloride is between 2 and 3 to 7.

3. The composition of claim 1 as a dry mixture.

4. The composition of claim 1 in an aqueous solution.

5. The composition of claim 1 wherein the succinic acid is included.

6. The composition of claim 1 wherein the weight ratio of lysine monohydrochloride to potassium chloride is between about 2 and 2.99 to 7 and the succinic acid is included in an amount between 0.1 and 10 percent by weight.

7. A method for imparting a salty taste to a food which comprises providing an edible composition in the food which consists essentially of an admixture selected from the group consisting of (1) lysine monohydrochloride and potassium chloride, and (2) lysine monohydrochloride, potassium chloride and succinic acid, each of which are food grade, wherein the ratio of lysine monohydrochloride to potassium chloride is between about 1 to 9 and 3 to 2, the weight ratio of lysine monohydrochloride to succinic acid is between about 3 to 1 and 13 to 1 and the composition has a pH between about 5.5 and 6.3.

8. The method of claim 7 wherein the weight ratio of lysine monohydrochloride to potassium chloride is 3 to 7.

9. The method of claim 7 wherein the succinic acid is included.

10. The method of claim 7 wherein the weight ratio of lysine monohydrochloride to potassium chloride is between about 2 and 2.99 to 7 and the succinic acid is included in an amount between 0.1 and 10 percent by weight.

* * * * *